(12) United States Patent
Wisniewski et al.

(10) Patent No.: US 8,148,319 B2
(45) Date of Patent: Apr. 3, 2012

(54) PEPTIDIC VASOPRESSIN RECEPTOR AGONISTS

(75) Inventors: Kazimierz Wisniewski, San Diego, CA (US); Claudio Schteingart, San Diego, CA (US); Regent Laporte, San Diego, CA (US); Robert Felix Galyean, Escondido, CA (US); Pierre Riviere, San Diego, CA (US)

(73) Assignee: Ferring B.V. (NL)

( * ) Notice: Subject to any disclaimer, the term of this patent is extended or adjusted under 35 U.S.C. 154(b) by 975 days.

(21) Appl. No.: 11/659,215

(22) PCT Filed: Aug. 3, 2005

(86) PCT No.: PCT/US2005/027772
§ 371 (c)(1),
(2), (4) Date: Jun. 2, 2008

(87) PCT Pub. No.: WO2006/020491
PCT Pub. Date: Feb. 23, 2006

(65) Prior Publication Data
US 2009/0054309 A1    Feb. 26, 2009

Related U.S. Application Data

(60) Provisional application No. 60/600,377, filed on Aug. 11, 2004.

(30) Foreign Application Priority Data

Aug. 11, 2004  (EP) .................................. 04019029

(51) Int. Cl.
*A61K 38/12* (2006.01)
(52) U.S. Cl. ........................... 514/1.1; 530/317
(58) Field of Classification Search .................. None
See application file for complete search history.

(56) References Cited

U.S. PATENT DOCUMENTS

| | | | |
|---|---|---|---|
| 3,352,843 A | 11/1967 | Boissonnas et al. | |
| 4,483,794 A | 11/1984 | Barth et al. | |
| 5,459,236 A | 10/1995 | Aurell et al. | |
| 5,516,795 A * | 5/1996 | Dellaria et al. | 514/467 |
| 6,262,021 B1 | 7/2001 | Uvnas-Moberg et al. | |
| 2003/0109670 A1 * | 6/2003 | Olivera et al. | 530/324 |
| 2004/0009550 A1 | 1/2004 | Moll et al. | |

FOREIGN PATENT DOCUMENTS

| | | |
|---|---|---|
| CS | 235151 | 2/1987 |
| CS | 242 062 | 2/1988 |
| EP | 1 027 067 | 9/2004 |
| EP | 1 406 649 | 2/2008 |
| RU | 2 063 979 | 7/1996 |
| RU | 2 342 949 | 1/2009 |
| WO | WO 89/03393 | 4/1989 |
| WO | WO 91/13092 | 9/1991 |
| WO | WO 88/01163 | 2/1998 |
| WO | WO 99/46283 | 9/1999 |
| WO | WO 02/064740 | 8/2002 |
| WO | WO 03/082334 | 10/2003 |
| WO | WO 03/099862 | 12/2003 |
| WO | WO 2004/030524 | 4/2004 |

OTHER PUBLICATIONS

O'Brien et al., "Terlipressin for Norepinephrine-Resistant Septic Shock," *The Lancet*, vol. 359, Apr. 2002, pp. 1209-1210.
Chen. "Vasopressin: New Uses in Critical Care." *Southwestern Internal Medicine Conference*. vol. 324. No. 3. 2002. pp. 146-154.
Jolley et al. "Terlipression Infusion in Catecholamine-resistant shock." *Anaesth. Intensive Care*. Col. 31. 2003. pp. 560-564.
Lauzier et al. "Vasopressin in the treatment of septic shock." *Reanimation*. vol. 13. 2004. pp. 147-153. Abstract.
Moreau et al. "Comparison of the effect of terlipression and albumin on arterial blood volume in patients with cirrhosis and tense ascites treated by paracentesis: a radomised pilot study." *Gut*. vol. 50. 2002. pp. 90-94.
Morelli et al. "Effects of terlipressin on systemic and regional haemodynamis in catecholamine-treated hyperkinetic septic shock." *Intensive Care Med*. vol. 30. 2004. pp. 597-604.
O'Brien et al. "Terlipression for nonrepinephrine-resistant septic shock." *The Lancet*. vol. 459. 2002. pp. 1209-1210.
Reid. "Role of Vasopression deficiency in the vasodilation of septic shock." *Circulation*. vol. 95. 1997. pp. 1108-1110.
Terrillon et al. "Synthesis and Characterization of Fluorescent Antagonists and Agonist for Human Oxytocin Vasopression $V_{1a}$ Receptors." *J. Med. Chem*. vol. 45. 2002. pp. 2579-2588.
Wisniewski et al. "The efficient synthesis of FMOC-1-homoglutamine." *Oppi Briefs*. vol. 29. No. 3. 1997. pp. 338-341.
Derwent Abstract—XP-002312063.

* cited by examiner

*Primary Examiner* — Christopher R. Tate
*Assistant Examiner* — Roy Teller
(74) *Attorney, Agent, or Firm* — Fish & Richardson P.C.

(57) ABSTRACT

The present invention relates to novel compounds, pharmaceutical compositions comprising the same, use of said compounds for the manufacture of a medicament for treatment of inter alia shock conditions as well as to a method for treatment of said conditions, wherein said compounds are administered. The compounds are represented by the general formula (I), as further defined in the specification.

16 Claims, No Drawings

PEPTIDIC VASOPRESSIN RECEPTOR AGONISTS

CROSS REFERENCE TO RELATED APPLICATIONS

This application is the National Phase of PCT/US2005/027772, filed Aug. 3, 2005, and published as WO 2006/020491, which in turn claims priority to European Patent Application No. 04019029.0, filed Aug. 11, 2004, and U.S. Provisional Application No. 60/600,377, filed Aug. 11, 2004, the entirety of these applications are incorporated herein by reference.

FIELD OF THE INVENTION

The present invention relates to novel compounds, pharmaceutical compositions comprising the same, use of said compounds for the manufacture of a medicament for treatment of inter alia shock conditions as well as to a method for treatment of said conditions, wherein said compounds are administered.

BACKGROUND

Peptidic vasopressin V1a receptor agonists, such as terlipressin, have recently (see e.g. O'Brian et al., Lancet 359 (9313):1209-10, Jun. 4, 2002) received increased attention for clinical use in treatment of critical care diseases and conditions, including shock of hypovolemic (e.g. hemorrhagic) or vasodilatory (e.g. septic) origin, bleeding esophageal varices (BEV), hepatorenal syndrome (HRS), cardiopulmonary resuscitation and anesthesia-induced hypotension. They have also been shown to have clinical use in the treatment of orthostatic hypotension, paracentesis-induced circulatory dysfunction, intra-operative blood loss and blood loss associated with burn débridement and epistaxis, and for treatment of various ocular diseases by increasing lacrimation/tear formation.

In treating critical care conditions it is highly desirable to control the arterial blood pressure, and the drug used is typically administered intravenously. Continuous intravenous drug infusion at increasing or decreasing rates is a practical means of providing the desired degree of control. The attainment of so-called "steady state" plasma concentrations of drug depends on the elimination half life of the drug infused. It is generally recognised that steady state plasma concentration is achieved after a period of time equivalent to three times the elimination half life of the drug. To be practical in a clinical setting the desired arterial blood pressure at the steady state should be attained in about two hours, preferably in one hour or less. V1a agonists with an elimination half life longer than 1 hour are therefore usually not considered useful for critical care treatment.

A disadvantage of terlipressin in many critical care situations is its long duration of action, which makes it difficult to titrate its effect as the disease state changes. The efficacy of terlipressin at the human V1a (hV1a) receptor also needs to be improved e.g. to allow lower dosages in general.

Also the compound known as F180 (cf. example 3 in U.S. Pat. No. 5,459,236) has an inconveniently long duration of action to be considered for the treatment of most critical care conditions.

Non-specific receptor agonist activity is the main disadvantage of other existing compounds, e.g. [Phe2,Orn8]OT (cf. example 1f in U.S. Pat. No. 3,352,843) and arginine-vasopressin (AVP). Activity at related receptors such as V1b, V2 and oxytocin (OT) receptors may potentially generate undesirable side effects and safety concerns. As an example, V2 receptor activation may induce antidiuresis (cf. desmopressin), release of coagulation/thrombolysis factors, and induce vasodilation/hypotension with reflex tachycardia. The latter side effect may also be induced by OT receptor agonist activity.

It is an objective of the present invention to provide compounds that are especially useful in the treatment of critical care conditions.

DISCLOSURE OF THE INVENTION

The present invention relates to compounds represented by the general formula (I) (SEQ ID NO: 53):

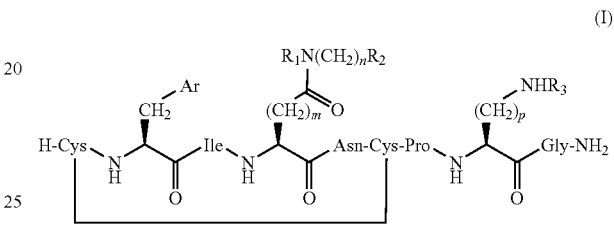

(I)

wherein:
Ar is an aryl group selected from aromatic carbocyclic ring systems, five- or six-membered heteroaromatic ring systems and bicyclic heteroaromatic ring systems;
m is selected from 1, 2 and 3;
n is selected from 0, 1, 2, 3 and 4;
p is selected from 2, 3 and 4;
$R_1$, $R_2$ and $R_3$ are independently selected from H, OH, alkyl, O-alkyl and OC(O)-alkyl;
alkyl is selected from $C_{1-6}$ straight and $C_{4-8}$ branched chain alkyl and optionally has at least one hydroxyl substituent;
and when n=0, $R_1$ and $R_2$ optionally together form a nitrogen containing ring structure comprising from 2 to 5 carbon atoms;
with the proviso that when Ar is phenyl (amino acid no. 2 is Phe), m=2, n=0 and $R_1=R_2=H$ (amino acid no. 4 is Gln) $R_3$ is not H when p is 3 or 4; and
solvates and pharmaceutically acceptable salts thereof.
Amino acid no. 8 is Orn when $R_3=H$ and p=3, and Lys when $R_3=H$ and p=4.

For the purposes of the present invention, the following terminology is used.

Aromatic carbocyclic ring systems includes phenyl and naphthyl.

A five-membered heteroaromatic ring system is a monocyclic aromatic ring system having five ring atoms, wherein 1, 2 or 3 ring atoms are independently selected from N, O and S. Preferred such ring systems are selected form a group consisting of thienyl, furyl, pyrrolyl, imidazolyl, thiazolyl, oxazolyl, pyrazolyl, isothiazolyl, isoxazolyl and tetrazolyl.

A six-membered heteroaromatic ring system is a monocyclic aromatic ring system having six ring atoms, wherein 1, 2 or 3 ring atoms are independently selected from N, O and S. It is preferably selected from a group consisting of pyridyl, pyrazinyl, pyrimidinyl, triazinyl and pyridazinyl.

A bicyclic heteroaromatic ring system is a ring system having two five- or six-membered heteroaromatic rings, or a phenyl and a five- or six-membered heteroaromatic ring, or a phenyl and a heterocyclyl ring, or a five- or six-membered heteroaromatic ring and a heterocyclyl ring; connected by a ring fusion, said bicyclic heteroaromatic ring system comprising 8 to 12 ring atoms, wherein 1, 2 or 3 of the ring atoms are independently selected from N, O and S. It is preferably selected from a group consisting of indole, quinoline, tetrahydroquinoline, isoquinoline, tetrahydroisoquinoline, 1,4-benzodioxan, coumarin, benzofuran, 1,2-benzisoxazole, benzothiophene, benzoxazole, benzthiazole, benzimidazole, benztriazole, pyrolizidine and quinolizidine.

A heterocyclyl or heterocyclic moiety is a saturated or partially saturated ring system having 3 to 7 ring atoms, wherein 1, 2 or 3 ring atoms are independently selected from N, O and S. Heterocyclyl moieties are preferably selected from a group consisting of aziridine, oxirane, thiirane, azetidine, oxetane, thietane, pyrrolidine, pyrroline, imidazolidine, pyrazolidine, dioxolane, tetrahydrofuranyl, piperidine, piperazine, morpholine, tetrahydropyranyl, 1,4-dioxanyl, homopiperidinyl, homopiperazinyl and hexamethylene oxide.

It deserves mentioning that e.g. also isopropyl and 2-n-butyl groups are encompassed by the expression $C_{1-6}$ straight chain alkyl, as said expression is not related to the binding site of the straight chain in question.

$C_{1-6}$ denotes having from one to six carbon atoms, including any number therebetween, and this nomenclature is used analogously herein.

Examples of pharmaceutically acceptable salts comprise acid addition salts, e.g. a salt formed by reaction with hydrohalogen acids, such as hydrochloric acid, and mineral acids, such as sulphuric acid, phosphoric acid and nitric acid, as well as aliphatic, alicyclic, aromatic or heterocyclic sulphonic or carboxylic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybenzoic acid, embonic acid, methanesulphonic acid, ethanesulphonic acid, hydroxyethanesulphonic acid, halobenzenesulphonic acid, toluenesulphonic acid and naphtalenesulphonic acid.

Ar is preferably selected from phenyl, 2- or 3-thienyl, 2- or 3-furyl, 2-, 3- or 4-pyridyl and 2-, 4- or 5-thiazolyl. It is particularly preferred that $R_1$ is H.

In preferred embodiments p is 2 or 3.

It is preferred to select $R_2$ from H, OH, $CH_3$, $CH_2CH_3$, $CH(CH_3)_2$, $CH(CH_2OH)_2$, $CH(OH)CH_3$ (both enantiomers), $OCH_3$ and $OCH_2CH_2OH$.

Moreover, it is preferred to select $R_3$ from H, methyl, ethyl, n-propyl, i-propyl and i-amyl.

In the most preferred embodiment, said compound having the formula (I) is selected from a group consisting of (SEQ ID NOs: 1-7, respectively, in order of appearance):

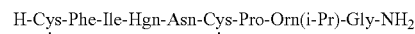 (1)

H-Cys-Phe-Ile-Hgn-Asn-Cys-Pro-Orn(i-Pr)-Gly-NH$_2$

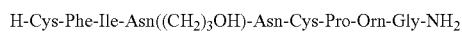 (2)

H-Cys-Phe-Ile-Asn((CH$_2$)$_3$OH)-Asn-Cys-Pro-Orn-Gly-NH$_2$

 (3)

H-Cys-Phe-Ile-Asn-Asn-Cys-Pro-Dbu-Gly-NH$_2$

 (4)

H-Cys-Phe-Ile-Asn-(CH$_2$CH$_3$)-Asn-Cys-Pro-Dbu-Gly-NH$_2$

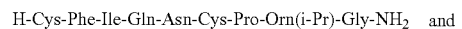 (5)

H-Cys-Phe-Ile-Gln-Asn-Cys-Pro-Orn(i-Pr)-Gly-NH$_2$ and

 (6)

H-Cys-Phe-Ile-Gln-Asn-Cys-Pro-Orn(CH$_2$CH$_3$)-Gly-NH$_2$,

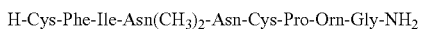 (7)

H-Cys-Phe-Ile-Asn(CH$_3$)$_2$-Asn-Cys-Pro-Orn-Gly-NH$_2$

The number in parenthesis denotes the compound as referred to in the following.

Furthermore the present invention relates to a compound as set forth above for use as a pharmaceutical.

Accordingly, the present invention also relates to a pharmaceutical composition comprising a compound as set forth above as active ingredient in association with a pharmaceutically acceptable adjuvant, diluent or carrier.

The pharmaceutical composition may be adapted for oral, intravenous, topical, intraperitoneal, nasal, buccal, sublingual or subcutaneous administration or for administration via the respiratory tract e.g. in the form of an aerosol or an air-suspended fine powder. The composition may thus for instance be in the form of tablets, capsules, powders, microparticles, granules, syrups, suspensions, solutions, transdermal patches or suppositories.

It should be noted that the composition according to the present invention may optionally include two or more of the above outlined compounds.

The present pharmaceutical composition may optionally comprise e.g. at least one further additive selected from a disintegrating agent, binder, lubricant, flavoring agent, preservative, colorant and any mixture thereof. Examples of such and other additives are found in "*Handbook of Pharmaceutical Excipients*"; Ed. A. H. Kibbe, 3$^{rd}$ Ed., American Pharmaceutical Association, USA and Pharmaceutical Press UK, 2000.

The present pharmaceutical composition is most preferably adapted for parenteral administration. It may comprise a sterile aqueous preparation of the compounds of the invention preferably isotonic with the blood of the recipient. This aqueous preparation may be formulated according to known methods using suitable dispersing or wetting agents and suspending agents. The injectable aqueous formulation Remestyp® (terlipressin) is exemplary of a suitable pharmaceutical formulation. The preparation may also be a sterile injectable solution or suspension in a diluent or solvent, for example as a solution in 1,3-butane diol. Water, Ringer's solution, and isotonic sodium chloride solution are exemplary acceptable diluents. Sterile, fixed oils may be employed as a solvent or suspending medium. Bland fixed oils, including synthetic mono or di-glycerides, and fatty acids, such as oleic acid, may also be used.

In addition, the present invention relates to use of a compound as outlined above for the manufacture of a medicament for treatment of shock of hypovolemic or vasodilatory origin, BEV, HRS, cardiopulmonary resuscitation, anesthesia-induced hypotension, orthostatic hypotension, paracentesis-induced circulatory dysfunction, intra-operative blood loss or blood loss associated with burn débridement and epistaxis, and for treatment of various ocular diseases by increasing lacrimation/tear formation.

In another embodiment the invention relates to a method for treatment of shock of hypovolemic or vasodilatory origin, BEV, HRS, cardiopulmonary resuscitation, anesthesia-induced hypotension, orthostatic hypotension, paracentesis-induced circulatory dysfunction, intra-operative blood loss or blood loss associated with burn débridement and epistaxis, and of various ocular diseases by increasing lacrimation/tear formation, wherein said method comprises administering to an animal, including human, patient of a therapeutically effective amount of a compound as outlined above.

The typical dosage of the compounds according to the present invention varies within a wide range and will depend on various factors such as the individual needs of each patient and the route of administration. The dosage administered by infusion is generally within the range of 0.01-200 μg/kg body weight per hour. A physician of ordinary skill in the art will be able to optimise the dosage to the situation at hand.

The abbreviations used are:
Abu 2-aminobutyric acid
Boc tert-butoxycarbonyl
BOP benzotriazol-1-yloxy trisdimethylaminophosphonium hexafluorophosphate
Dbu 2,4-diaminobutyric acid
DCC N,N'-dicyclohexylcarbodiimide
DCHA dicyclohexylamine
DCM dichloromethane
DIAD diisopropyl diazodicarboxylate
DIC N,N'-diisopropylcarbodiimide
DIEA N, N-diisopropyl-N-ethylamine
DMF N,N-dimethylformamide
Fm 9-fluorenylmethyl
Fmoc 9-fluorenylmethoxycarbonyl
Hgn homoglutamine
Hmp 2-hydroxy-3-mercaptopropionic acid
HOBt 1-hydroxybenzotriazole
HPLC high performance liquid chromatography
i iso
Mmt 4-methoxytrityl
Mob p-methoxybenzyl
MS mass spectrometry
Orn ornithine
Ph phenyl
Pr propyl
PyBOP benzotriazol-1-yloxy trispyrrolidinephosphonium hexafluorophosphate
o-NBS-Cl 2-nitrobenzenesulfonyl chloride
OT oxytocin
Rt retention time
TFA trifluoroacetic acid
TIS triisopropylsilane
TMOF trimethylorthoformate
TPP triphenylphosphine
Trt trityl
VT vasotocin, [Ile$^3$]vasopressin Unless otherwise specified L-amino acids were used, and conventional amino acid terminology is adhered to.

Experimental (Synthesis)

Amino acid derivatives and resins were purchased from commercial providers (Novabiochem, Bachem Peptide International and PepTech Corporation). Fmoc-Hgn-OH was synthesised according to literature (Wisniewski, K., Kolodziejczyk, A. S. *Org. Prep. Proced. Int.* 1997, 29, 338-341). Other chemicals and solvents were provided from Sigma-Aldrich, Fisher Scientific and VWR.

The compounds herein were synthesised by standard methods in solid phase peptide chemistry utilising both Fmoc and Boc methodology. Unless otherwise provided, all reactions were performed at room temperature. In addition to the references cited supra, the following standard reference literature provides further guidance on general experimental set up, as well as on the availability of required starting material and reagents:

Kates, S. A., Albericio, F., Eds., *Solid Phase Synthesis. A Practical Guide*, Marcel Dekker, New York, Basel, 2000;

Stewart, J. M., Young, J. D. *Solid Phase Synthesis*, Pierce Chemical Company, 1984;

Bisello, et al., *J. Biol. Chem.* 1998, 273, 22498-22505; and

Merrifield, *J. Am. Chem. Soc.* 1963, 85, 2149-2154.

Purity of the synthesized peptide may be determined by analytical reversed phase HPLC. Structural integrity of the peptides may be confirmed using amino acid analysis and electrospray mass spectrometry.

The peptides synthesised by Fmoc methodology were cleaved with a TFA/TIS/H$_2$O 96/2/2 (v/v/v) solution, and cleavage in Boc methodology was accomplished with 90% HF/10% anisole (v/v) solution. Disulfide bridge (ring) formation was achieved by oxidation of linear peptides dissolved in 10% TFA (aq) with iodine. Peptides were purified by preparative HPLC in triethylammonium phosphate buffers (aq). The compounds were finally converted to acetate salts using conventional HPLC methodology. The fractions with a purity exceeding 97% were pooled and lyophilised.

Synthesis of Peptides with Alkylated Side Chain in Position No. 8:

The peptides were assembled with Fmoc methodology. The diamino acid residue in position no. 8 was introduced with an acid labile (i.e. removable with a solution containing 1-2% TFA) protecting group, such as methoxy-trityl (Mmt; see Barlos, K. et al. in *Peptides* 1992, Schneider, C. H., Eberle, A. N., Eds., ESCOM Science Publishers B. V., 1993, pp 283-284). Resin bound peptide was treated with a DCM/TIS/TFA 93/5/2 (v/v/v) solution for the Mmt group removal. Reductive alkylation with acetone/NaBH(OAc)$_3$ provided the N-isopropyl peptide.

To avoid undesirable N,N-dialkylation in reductive alkylation in the above procedure, which may occur when straight chain alkyl aldehydes are used, an alternative was developed, wherein after the Mmt removal the amino group was first derivatised with 2-nitrobenzenesulfonyl chloride (o-NBS-Cl; see Fukuyama, T.; Jow, C.-K.; Cheung, M. *Tetrahedron Lett.* 1995, 36, 6373-6374). The resulting sulphonamide was then alkylated with an appropriate alcohol under conventional Mitsunobu reaction conditions, typically utilising TPP/DIAD in 1,2-dimethoxyethane (Mitsunobu, O. *Synthesis* 1981, 1-28). The o-NBS-Cl group was subsequently removed with 5% potassium thiophenolate in DMF, after which the peptide was cleaved from the resin.

Synthesis of Peptides with N-alkylated Side Chain in Position No. 4:

The peptides were assembled with Boc methodology. The residue in position no. 4 was introduced in the sequence as Boc-Asp(OFm)-OH. After complete peptide assembly the side chain protection was removed with 30% piperidine in DMF. The resulting free carboxylic group was converted to the desired amide by coupling with an appropriate amine mediated by PyBOP or BOP/DIEA. The N-terminal Boc group was then removed, followed by HF cleavage, cyclisation and purification by HPLC.

Table 1 lists the compounds prepared by the above procedure. $R_1$ is H for all compounds except no. 7, where $R_1$ is $CH_3$. An asterisk "*" marks the most preferred embodiments.

TABLE 1

Compounds prepared with the formula (I)

| Substituent | | | | | | Denoted SEQ ID NO |
|---|---|---|---|---|---|---|
| Ar | m | n | $R_2$ | P | $R_3$ | |
| Ph | 2 | 0 | H | 2 | H | 8 |
| Ph | 3 | 0 | H | 3 | H | 9 |
| Ph | 2 | 0 | $OCH_3$ | 3 | H | 10 |
| Ph | 3 | 0 | H | 2 | H | 11 |
| 4-pyridyl | 2 | 0 | H | 2 | H | 12 |
| 4-thiazolyl | 2 | 0 | H | 2 | H | 13 |
| 2-thienyl | 2 | 0 | H | 2 | H | 14 |
| 3-thienyl | 2 | 0 | H | 2 | H | 15 |
| Ph | 2 | 0 | OH | 3 | H | 16 |
| 2-pyridyl | 2 | 0 | H | 2 | H | 17 |
| 3-pyridyl | 2 | 0 | H | 2 | H | 18 |
| Ph | 2 | 0 | $CH_3$ | 3 | H | 19 |
| Ph | 2 | 1 | $CH_3$ | 3 | H | 20 |
| Ph | 2 | 1 | $CH(CH_3)_2$ | 3 | H | 21 |
| Ph | 3 | 0 | H | 3 | $CH(CH_3)_2$ | 1* |
| Ph | 3 | 0 | H | 2 | $CH(CH_3)_2$ | 22 |
| Ph | 1 | 2 | OH | 3 | H | 23 |
| Ph | 1 | 0 | OH | 3 | H | 24 |
| 2-furyl | 2 | 0 | H | 3 | H | 25 |
| Ph | 1 | 3 | OH | 3 | H | 2* |
| 2-furyl | 2 | 0 | H | 2 | H | 26 |
| Ph | 1 | 0 | $CH(CH_2OH)_2$ | 3 | H | 27 |
| Ph | 1 | 1 | $CH(OH)CH_3$ | 3 | H | 28 |
| Ph | 1 | 2 | $OCH_2CH_2OH$ | 3 | H | 29 |
| Ph | 1 | 0 | H | 3 | H | 30 |
| Ph | 1 | 0 | H | 2 | H | 3* |
| Ph | 1 | 0 | $CH_3$ | 2 | H | 31 |
| Ph | 1 | 1 | $CH_3$ | 2 | H | 4* |
| 2-furyl | 2 | 0 | H | 3 | H | 32 |
| 2-thienyl | 1 | 0 | H | 3 | H | 33 |
| Ph | 2 | 0 | H | 3 | $CH(CH_3)_2$ | 5* |
| 2-thienyl | 2 | 0 | H | 3 | $CH(CH_3)_2$ | 34 |
| 3-thienyl | 1 | 0 | H | 3 | H | 35 |
| 2-thienyl | 1 | 0 | H | 2 | H | 36 |
| 3-thienyl | 1 | 0 | H | 2 | H | 37 |
| 2-furyl | 1 | 0 | H | 3 | H | 38 |
| Ph | 2 | 0 | H | 3 | $CH_3$ | 39 |
| Ph | 2 | 0 | H | 3 | $CH_2CH_2CH_3$ | 40 |
| Ph | 1 | 0 | H | 3 | $CH(CH_3)_2$ | 41 |
| 2-furyl | 1 | 0 | H | 3 | $CH(CH_3)_2$ | 42 |
| 2-thienyl | 1 | 0 | H | 3 | $CH(CH_3)_2$ | 43 |
| 2-furyl | 1 | 0 | H | 2 | H | 44 |
| Ph | 2 | 0 | H | 3 | $CH_2CH_3$ | 6* |
| Ph | 2 | 0 | H | 3 | $(CH_2)_2CH(CH_3)_2$ | 45 |
| Ph | 1 | 0 | H | 3 | $CH_3$ | 46 |
| Ph | 1 | 0 | H | 3 | $CH_2CH_3$ | 47 |
| Ph | 1 | 0 | $CH_3$ | 3 | H | 7* |
| Ph | 1 | 1 | $CH_3$ | 3 | H | 48 |
| Ph | 1 | 0 | $CH_3$ | 3 | H | 49 |
| Ph | 1 | 0 | H | 3 | $CH_2CH_2CH_3$ | 50 |

The following detailed examples are provided to further illustrate the synthesis:

Compound 1; [Phe², Hgn⁴, Orn(i-Pr)⁸]VT:

The amino acid derivatives used were Boc-Cys(Trt)-OH, Fmoc-Phe-OH, Fmoc-Ile-OH, Fmoc-Hgn-OH, Fmoc-Asn (Trt)-OH, Fmoc-Cys(Trt)-OH, Fmoc-Pro-OH, Fmoc-Orn (Mmt)-OH and Fmoc-Gly-OH. Fmoc-Hgn-OH was synthesised as mentioned above. Analytical HPLC was performed on a Waters 600 Liquid Chromatograph using a Vydac C18, 5µ 4.6×250 mm, column at a flow rate of 2 ml/min. Preparative HPLC was performed on a Waters 2000 Liquid Chromatograph using a Prepak 47×300 mm cartridge at a flow rate of 100 ml/min. Final compound analysis was performed on a 1100 Agilent Liquid Chromatograph using a Vydac C18, 5µ 2.1×250 mm, column at a flow rate of 0.3 ml/min. Mass spectra were recorded on a Finnigan MAT spectrometer.

The fully protected peptide resin was synthesised on an Applied Biosystems 9050 Peptide Synthesiser starting from 2 g (0.5 mmol) of Tentagel-S-RAM resin (Peptides International). DIC/HOBt mediated single couplings with a 4-fold excess of amino acid derivatives were performed. The Fmoc group was removed with 20% piperidine in DMF. Upon completion of the automated synthesis, the resin was transferred into a manual synthesis vessel and was treated with DCM/TIS/TFA 93/5/2 (v/v/v) solution (30 ml) for 2×1.5 hours for removal of the Mmt group. The resin was thoroughly washed with DCM and was subsequently suspended in 15 ml of 1,2-dichloroetehane/TMOF 1:1 (v/v). 0.2 ml of acetone was then added followed by 0.6 g of $NaBH(OAc)_3$. The suspension was shaken overnight and the resin was washed with methanol, DMF and DCM and dried in vacuo. The resin was then treated with 30 ml of the $TFA/TIS/H_2O$ 96/2/2 (v/v/v) solution for 1.5 hours and filtered off. The filtrate was evaporated and the crude linear peptide was precipitated with diethyl ether. The precipitate was immediately dissolved in 500 ml of 10% TFA (aq), and the peptide was oxidised by adding 0.1 M $I_2$ in methanol to the magnetically stirred solution until yellow color persisted. Excess of iodine was reduced with ascorbic acid. The reaction mixture was then cooled with crushed ice and pH was adjusted to about 5 by adding concentrated ammonia (aq). The mixture was loaded onto an HPLC column and purified using a triethylammonium phosphate buffer with pH 5.2. The compound was eluted with a gradient of acetonitrile. The fractions with a purity exceeding 97% were pooled, and the resulting solution was diluted with 2 volumes of water. The solution was reloaded onto the column which was then washed with 2 l of 0.1 M ammonium acetate (aq) and equilibrated with 2% acetic acid (aq). The compound was eluted with a fast (3%/min) gradient of acetonitrile. The fractions containing the desired product were pooled and lyophilised. 168 mg (~30% yield) of white amorphous powder was obtained. HPLC: Rt=8.5 min, gradient: 20→40% B over 20 min, t=40° C., solvent A 0.01% TFA (aq), solvent B 70% $CH_3CN$, 0.01% TFA (aq); Purity: 98.8%; MS (M+H⁺): expected 1048.5, observed 1048.5.

Compound 4; [Phe², Asn(Et)⁴, Dbu⁸]VT:

The amino acid derivatives used were Boc-Cys(Mob)-OH, Boc-Phe-OH, Boc-Ile-OH, Boc-Asp(OFm)-OH, Boc-Asn-OH, Boc-Pro-OH, Boc-Dbu(benzyloxycarbonyl)-OH DCHA salt and Boc-Gly-OH, all purchased from Novabiochem and Bachem. HPLC and MS operations were performed as in the synthesis of compound 1.

The fully protected peptide resin was manually synthesised starting from 0.6 g (0.4 mmol) of 4-methyl-benzhydrylamine resin (Novabiochem). DCC, PyBOP or DIC/HOBt mediated single couplings with 2.5-fold excess of amino acid derivatives were employed. The Boc group was removed with 50% TFA in DCM containing 1% of m-cresol. Upon completion of the synthesis, the 9-fluorenylmethyl ester was removed from the β-carboxylic group of aspartic acid by treatment with 30% piperidine in DMF for 2×30 min. The resin was washed with 1 M HOBt in DMF solution for 30 min and then twice with DMF only. The free carboxylic group was amidated by overnight treatment with 2 mmol of ethylamine/PyBOP/DIEA in DMF. The finished resin was washed with methanol, DMF and DCM and dried in vacuo. The peptide was cleaved from the resin by using 30 ml of anhydrous HF containing 3 ml of anisole at 0° C. for 90 minutes. The HF was evaporated off, and the crude linear peptide was washed with diethyl ether. The peptide was immediately dissolved in 200 ml of 25% acetonitrile/10% TFA (aq) and oxidised as described supra. The resulting mixture was loaded directly onto an HPLC column and purified using triethylammonium phosphate buffer at pH 2.3. The subsequent purification steps were identical to the procedure for compound 1. 41 mg (~10% yield) of white amorphous powder was obtained. HPLC: Rt=10.0 min, gradient: 20→40% B over 20 min, t=40° C., solvent A 0.01% TFA (aq), solvent B 70% CH$_3$CN, 0.01% TFA (aq); Purity: 100%; MS (M+H$^+$): expected 992.5, observed 992.2.

The other compounds were prepared by analogous variation of these synthetic procedures.

Experimental (Biological Testing)

In vitro Receptor Assays:

Agonist activity of compounds on the hV1a receptor was determined in a transcriptional reporter assay by transiently transfecting a hV1a receptor expression DNA into HEK-293 cells in concert with a reporter DNA containing intracellular calcium responsive promoter elements regulating expression of firefly luciferase. See Boss, V., Talpade, D. J., Murphy, T. J. *J. Biol. Chem.* 1996, May 3; 271(18), 10429-10432 for further guidance on this assay. Cells were exposed to serial dilutions of compounds diluted 10-fold per dose for 5 hours, followed by lysis of cells, determination of luciferace activity, and determination of compound efficacies and EC$_{50}$ values through non-linear regression. Arginine-vasopressin (AVP) was used as an internal control in each experiment, and compounds were tested in at least three independent experiments. To determine selectivity, compounds were tested in luciferase-based transcriptional reporter assays expressing the human oxytocin (hOT) receptor. Assays for other receptors (hV2, hV1b, rat V1a and rat V2) were also conducted.

For further comparative purposes, other reference compounds used were [Phe2,Orn8]OT, terlipressin and F180.

The structure of [Phe2,Orn8]OT is (SEQ ID NO: 51):

H-Cys-Phe-Ile-Gln-Asn-Cys-Pro-Orn-Gly-NH$_2$

The structure of F180 is (SEQ ID NO: 52):

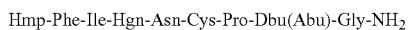

Hmp-Phe-Ile-Hgn-Asn-Cys-Pro-Dbu(Abu)-Gly-NH$_2$

The results of the in vitro assays are depicted in table 2 infra. The EC$_{50}$ value given is the geometric mean expressed in nanomol/L (nM). Selectivity values are given as EC$_{50}$ ratios.

In vivo Pharmacological Tests:

The compounds were tested in vivo for duration of action related to a standard dose of AVP. Blood pressure tests were carried out on anaesthetised Sprague-Dawley male rats (weighing 270-300 g) with catheterised jugular vein and carotid artery. The catheterised carotid artery was used to continuously monitor blood pressure and the jugular vein was used for administration of the compounds tested. Rats received intravenous injections of dibenamine prior to dosing to enhance their responsiveness to V1a receptor agonists (cf. Dekanski, J., *Br. J. Pharmacol.* 1952, 7, 567-572). The dosing procedure consisted of one intravenous injection of physiological saline followed by two consecutive injections of a standard dose of AVP (0.1 nmol/kg, ≈ED$_{70}$), and three to five increasing doses of a given compound selected to give at least a response comparable to the standard dose of AVP. Dosing intervals were set as time for the blood pressure to decrease to a stable baseline.

Determination of duration of action was based on the decay rate of diastolic arterial blood pressure transient increase. Specifically, for an exponential decay of plasma concentration, it can be shown that, if the response is measured beyond the distribution phase, the rate of decay near the EC$_{50}$ is linear and inversely proportional to the elimination half-life (Rowland, M. and Tozer, T. in "*Clinical Pharmacokinetics, Concepts and Applications*", 3$^{rd}$ ed., Lippincott Williams & Wilkins, Philadelphia, 1995).

To measure the response decay rate for a given compound, a dose was selected that gave an amplitude of response as similar as possible to the amplitude of response to the second injection of the standard dose of AVP. To normalise for inter-individual variation in V1a-responsiveness, the duration of action was expressed as the ratio of decay rate for this reference AVP response to the decay rate for the equieffective dose of compound for each rat tested. The results obtained for the compounds tested are set forth in table 2.

TABLE 2

Results of biological testing

| Compound tested | EC$_{50}$ hV1a receptor | in vivo duration relative to AVP | selectivity hOT/hV1a |
|---|---|---|---|
| 8 | 0.50 | — | 11 |
| 9 | 0.68 | 1.5 | + |
| 10 | 1.15 | 2.3 | 11 |
| 11 | 2.96 | 1.9 | + |
| 12 | 24.96 | — | + |
| 13 | 18.77 | — | + |
| 14 | 0.54 | — | 75 |
| 15 | 0.61 | 2.2 | 43 |
| 16 | 11.88 | — | + |
| 17 | 30.29 | — | + |
| 18 | 29.85 | — | + |
| 19 | 5.99 | 1.6 | + |
| 20 | 39.28 | — | + |
| 21 | 20.66 | — | + |
| 1* | 2.02 | 1.7 | + |
| 22 | 18.13 | — | + |
| 23 | 7.97 | — | + |
| 24 | 4.09 | — | + |
| 25 | 1.40 | 2.0 | 23 |
| 2* | 1.18 | 1.7 | + |
| 26 | 2.24 | 2.0 | 28 |
| 27 | 16.21 | — | + |
| 28 | 5.17 | — | + |
| 29 | 4.77 | — | + |
| 30 | 1.45 | 1.7 | + |
| 3* | 1.47 | 1.7 | + |
| 31 | 3.91 | — | + |
| 4* | 2.36 | 1.8 | + |
| 32 | 2.64 | 2.1 | 35 |
| 33 | 14.61 | — | + |
| 5* | 0.25 | 1.9 | 117 |
| 34 | 0.73 | 2.0 | 72 |
| 35 | 7.30 | — | + |
| 36 | 11.54 | — | + |
| 37 | 7.45 | — | + |
| 38 | 10.11 | — | + |
| 39 | 0.21 | 1.9 | 178 |
| 40 | 0.27 | 2.0 | 88 |
| 41 | 0.98 | 2.6 | 53 |
| 42 | 6.25 | — | + |
| 43 | 13.71 | — | + |
| 44 | 14.48 | — | + |
| 6* | 0.29 | 1.9 | 86 |
| 45 | 1.65 | — | 18 |
| 46 | 2.41 | 2.1 | + |
| 47 | 0.99 | 1.6 | + |
| 7* | 2.84 | — | + |

TABLE 2-continued

Results of biological testing

| Compound tested | EC$_{50}$ hV1a receptor | in vivo duration relative to AVP | selectivity hOT/hV1a |
|---|---|---|---|
| 48 | 5.70 | — | + |
| 49 | 3.58 | — | + |
| 50 | 1.52 | 2.4 | 43 |
| [Phe2, Orn8]OT | 0.15 | 1.9 | 60 |
| terlipressin | 82.08 | 9.1 | + |
| AVP | 0.21 | 0.9 | 108 |
| F180 | 0.56 | 3.8 | + |

— = not tested
+ = selective hV1a receptor agonist; EC$_{50}$ hOT/hV1a ratio not determined due to very low agonist efficacy (<30% compared to AVP) at the hOT receptor All references listed are to be regarded as an integral part of the present writ.

The invention claimed is:

1. A compound selected from a group consisting of compounds of the following formulae (SEQ ID NOs: 1-7, respectively, in order of appearance):

H-Cys-Phe-Ile-Hgn-Asn-Cys-Pro-Orn(i-Pr)-Gly-NH$_2$

H-Cys-Phe-Ile-Asn((CH$_2$)$_3$OH)-Asn-Cys-Pro-Orn-Gly-NH$_2$

H-Cys-Phe-Ile-Asn-Asn-Cys-Pro-Dbu-Gly-NH$_2$

H-Cys-Phe-Ile-Asn(CH$_2$CH$_3$)-Asn-Cys-Pro-Dbu-Gly-NH$_2$

H-Cys-Phe-Ile-Gln-Asn-Cys-Pro-Orn(i-Pr)-Gly-NH$_2$

H-Cys-Phe-Ile-Gln-Asn-Cys-Pro-Orn(CH$_2$CH$_3$)-Gly-NH$_2$ and

H-Cys-Phe-Ile-Asn(CH$_3$)$_2$-Asn-Cys-Pro-Orn-Gly-NH$_2$ and pharmaceutically acceptable salts thereof.

2. A compound or pharmaceutically acceptable salt thereof according to claim 1, having wherein the compound has the structural formula (SEQ ID NO:7):

H-Cys-Phe-Ile-Asn(CH$_3$)$_2$-Asn-Cys-Pro-Orn-Gly-NH$_2$.

3. A pharmaceutical composition comprising a compound or pharmaceutically acceptable salt thereof according to claim 1, and a pharmaceutically acceptable adjuvant, diluent or carrier.

4. A compound or pharmaceutically acceptable salt thereof according to claim 1, wherein the compound has the structural formula:

(SEQ ID NO: 1)

H-Cys-Phe-Ile-Hgn-Asn-Cys-Pro-Orn(i-Pr)-Gly-NH$_2$.

5. A compound or pharmaceutically acceptable salt thereof according to claim 1, wherein the compound has the structural formula:

(SEQ ID NO: 2)

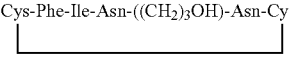

H-Cys-Phe-Ile-Asn-((CH$_2$)$_3$OH)-Asn-Cys-Pro-Orn-Gly-NH$_2$.

6. A compound or pharmaceutically acceptable salt thereof according to claim 1, wherein the compound has the structural formula:

(SEQ ID NO: 3)

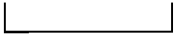

H-Cys-Phe-Ile-Asn-Asn-Cys-Pro-Dbu-Gly-NH$_2$.

7. A compound or pharmaceutically acceptable salt thereof according to claim 1, wherein the compound has the structural formula:

(SEQ ID NO: 4)

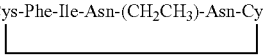

H-Cys-Phe-Ile-Asn-(CH$_2$CH$_3$)-Asn-Cys-Pro-Dbu-Gly-NH$_2$.

8. A compound or pharmaceutically acceptable salt thereof according to claim 1, wherein the compound has the structural formula:

H-Cys-Phe-Ile-Gln-Asn-Cys-Pro-Orn(i-Pr)-Gly-NH₂. (SEQ ID NO: 5)
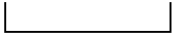

9. A compound or pharmaceutically acceptable salt thereof according to claim 1, wherein the compound has the structural formula:

H-Cys-Phe-Ile-Gln-Asn-Cys-Pro-Orn(CH₂CH₃)-Gly-NH₂. (SEQ ID NO: 6)

10. A method of treating a disorder in an animal, the method comprising administering to an animal patient in need of such treatment a therapeutically effective amount of a compound or pharmaceutically acceptable salt thereof according to claim 1, wherein the disorder is selected from the group consisting of shock of hypovolemic or vasodilatory origin, bleeding esophageal varices, hepatorenal syndrome, cardiopulmonary resuscitation, anesthesia-induced hypotension, orthostatic hypotension, paracentesis-induced circulatory dysfunction, intra-operative blood loss, blood loss associated with burn debridement, and blood loss associated with epistaxis.

11. A method according to claim 10, wherein the animal is a human.

12. A method according to claim 11, wherein the compound has the structural formula:

H-Cys-Phe-Ile-Hgn-Asn-Cys-Pro-Orn(i-Pr)-Gly-NH₂. (SEQ ID NO: 1)

13. A method according to claim 11, wherein the disorder is shock of hypovolemic origin.

14. A method according to claim 11, wherein the disorder is shock of vasodilatory origin.

15. A method according to claim 11, wherein the disorder is bleeding esophageal varices.

16. A method according to claim 11, wherein the disorder is hepatorenal syndrome.

* * * * *

UNITED STATES PATENT AND TRADEMARK OFFICE
CERTIFICATE OF CORRECTION

PATENT NO. : 8,148,319 B2
APPLICATION NO. : 11/659215
DATED : April 3, 2012
INVENTOR(S) : Kazimierz Wisniewski et al.

It is certified that error appears in the above-identified patent and that said Letters Patent is hereby corrected as shown below:

Title page, Col. 2, "Other Publications", Line 5; delete ""Terlipression" and insert -- Terlipressin --.

Title page, Col. 2, "Other Publications", Line 9; delete "terlipression" and insert -- terlipressin --.

Title page, Col. 2, "Other Publications", Line 11; delete "radomised" and insert -- randomised --.

Title page, Col. 2, "Other Publications", Line 14; delete "haemodynamis" and insert -- haemodynamics --.

Title page, Col. 2, "Other Publications", Line 16; delete ""Terlipression" and insert -- "Terlipressin --.

Title page, Col. 2, "Other Publications", Line 16; delete "nonrepinephrine" and insert -- norepinephrine --.

Title page, Col. 2, "Other Publications", Line 18; delete "Vasopression" and insert -- vasopressin --.

Title page, Col. 2, "Other Publications", Line 21; delete "Vasopression" and insert -- Vasopressin --.

Col. 40, Line 40, Claim 5; delete "Asn-$((CH_2)_3OH)$" and insert -- Asn$((CH_2)_3OH)$ --.

Col. 40, Line 61, Claim 7; delete "Asn-$(CH_2CH_3)$" and insert -- Asn$(CH_2CH_3)$ --.

Signed and Sealed this
Twenty-fifth Day of September, 2012

David J. Kappos
*Director of the United States Patent and Trademark Office*

SEQUENCE LISTING

```
<160> NUMBER OF SEQ ID NOS: 53

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Hgn
<220> FEATURE:
<221> NAME/KEY: MOD_RES
<222> LOCATION: (8)
<223> OTHER INFORMATION: Orn(i-Pr)

<400> SEQUENCE: 1

Cys Phe Ile Xaa Asn Cys Pro Xaa Gly
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Asn((CH2)3OH)
<220> FEATURE:
<221> NAME/KEY: MOD_RES
<222> LOCATION: (8)
<223> OTHER INFORMATION: Orn

<400> SEQUENCE: 2

Cys Phe Ile Asn Asn Cys Pro Xaa Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Dbu

<400> SEQUENCE: 3
```

```
Cys Phe Ile Asn Asn Cys Pro Xaa Gly
1               5
```

```
<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Asn(CH2CH3)
<220> FEATURE:
<221> NAME/KEY: MOD_RES
<222> LOCATION: (8)
<223> OTHER INFORMATION: Dbu

<400> SEQUENCE: 4

Cys Phe Ile Asn Asn Cys Pro Xaa Gly
1               5
```

```
<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn(i-Pr)

<400> SEQUENCE: 5

Cys Phe Ile Gln Asn Cys Pro Xaa Gly
1               5
```

```
<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn(CH2CH3)

<400> SEQUENCE: 6

Cys Phe Ile Gln Asn Cys Pro Xaa Gly
1               5
```

```
<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Asn(CH3)2
<220> FEATURE:
<221> NAME/KEY: MOD_RES
<222> LOCATION: (8)
<223> OTHER INFORMATION: Orn

<400> SEQUENCE: 7
```

```
Cys Phe Ile Asn Asn Cys Pro Xaa Gly
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Dbu

<400> SEQUENCE: 8

Cys Phe Ile Gln Asn Cys Pro Xaa Gly
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Hgn
<220> FEATURE:
<221> NAME/KEY: MOD_RES
<222> LOCATION: (8)
<223> OTHER INFORMATION: Orn

<400> SEQUENCE: 9

Cys Phe Ile Xaa Asn Cys Pro Xaa Gly
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Glu(NHOCH3)
<220> FEATURE:
<221> NAME/KEY: MOD_RES
<222> LOCATION: (8)
<223> OTHER INFORMATION: Orn

<400> SEQUENCE: 10

Cys Phe Ile Glu Asn Cys Pro Xaa Gly
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Hgn
<220> FEATURE:
<221> NAME/KEY: MOD_RES
```

```
<222> LOCATION: (8)
<223> OTHER INFORMATION: Dbu

<400> SEQUENCE: 11

Cys Phe Ile Xaa Asn Cys Pro Xaa Gly
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: 4-Pal
<220> FEATURE:
<221> NAME/KEY: MOD_RES
<222> LOCATION: (8)
<223> OTHER INFORMATION: Dbu

<400> SEQUENCE: 12

Cys Xaa Ile Gln Asn Cys Pro Xaa Gly
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Ala(4-Thz)
<220> FEATURE:
<221> NAME/KEY: MOD_RES
<222> LOCATION: (8)
<223> OTHER INFORMATION: Dbu

<400> SEQUENCE: 13

Cys Ala Ile Gln Asn Cys Pro Xaa Gly
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Thi
<220> FEATURE:
<221> NAME/KEY: MOD_RES
<222> LOCATION: (8)
<223> OTHER INFORMATION: Dbu

<400> SEQUENCE: 14

Cys Xaa Ile Gln Asn Cys Pro Xaa Gly
1               5

<210> SEQ ID NO 15
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: 3-Thi
<220> FEATURE:
<221> NAME/KEY: MOD_RES
<222> LOCATION: (8)
<223> OTHER INFORMATION: Dbu

<400> SEQUENCE: 15

Cys Xaa Ile Gln Asn Cys Pro Xaa Gly
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Glu(NHOH)
<220> FEATURE:
<221> NAME/KEY: MOD_RES
<222> LOCATION: (8)
<223> OTHER INFORMATION: Orn

<400> SEQUENCE: 16

Cys Phe Ile Glu Asn Cys Pro Xaa Gly
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: 2-Pal
<220> FEATURE:
<221> NAME/KEY: MOD_RES
<222> LOCATION: (8)
<223> OTHER INFORMATION: Dbu

<400> SEQUENCE: 17

Cys Xaa Ile Gln Asn Cys Pro Xaa Gly
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: 3-Pal
<220> FEATURE:
<221> NAME/KEY: MOD_RES
<222> LOCATION: (8)
<223> OTHER INFORMATION: Dbu

<400> SEQUENCE: 18

Cys Xaa Ile Gln Asn Cys Pro Xaa Gly
```

```
<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Gln(CH3)
<220> FEATURE:
<221> NAME/KEY: MOD_RES
<222> LOCATION: (8)
<223> OTHER INFORMATION: Orn

<400> SEQUENCE: 19

Cys Phe Ile Gln Asn Cys Pro Xaa Gly
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Gln(CH2CH3)
<220> FEATURE:
<221> NAME/KEY: MOD_RES
<222> LOCATION: (8)
<223> OTHER INFORMATION: Orn

<400> SEQUENCE: 20

Cys Phe Ile Gln Asn Cys Pro Xaa Gly
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Gln(i-Bu)
<220> FEATURE:
<221> NAME/KEY: MOD_RES
<222> LOCATION: (8)
<223> OTHER INFORMATION: Orn

<400> SEQUENCE: 21

Cys Phe Ile Gln Asn Cys Pro Xaa Gly
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Hgn
```

```
<220> FEATURE:
<221> NAME/KEY: MOD_RES
<222> LOCATION: (8)
<223> OTHER INFORMATION: Dbu(i-Pr)

<400> SEQUENCE: 22

Cys Phe Ile Xaa Asn Cys Pro Xaa Gly
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Asn(CH2CH2OH)
<220> FEATURE:
<221> NAME/KEY: MOD_RES
<222> LOCATION: (8)
<223> OTHER INFORMATION: Orn

<400> SEQUENCE: 23

Cys Phe Ile Asn Asn Cys Pro Xaa Gly
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Asn(OH)
<220> FEATURE:
<221> NAME/KEY: MOD_RES
<222> LOCATION: (8)
<223> OTHER INFORMATION: Orn

<400> SEQUENCE: 24

Cys Phe Ile Asn Asn Cys Pro Xaa Gly
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Ala(2-Fur)
<220> FEATURE:
<221> NAME/KEY: MOD_RES
<222> LOCATION: (8)
<223> OTHER INFORMATION: Orn

<400> SEQUENCE: 25

Cys Ala Ile Gln Asn Cys Pro Xaa Gly
1               5

<210> SEQ ID NO 26
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Ala(2-Fur)
<220> FEATURE:
<221> NAME/KEY: MOD_RES
<222> LOCATION: (8)
<223> OTHER INFORMATION: Dbu

<400> SEQUENCE: 26

Cys Ala Ile Gln Asn Cys Pro Xaa Gly
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Asp(CH(CH2OH)2)
<220> FEATURE:
<221> NAME/KEY: MOD_RES
<222> LOCATION: (8)
<223> OTHER INFORMATION: Orn

<400> SEQUENCE: 27

Cys Phe Ile Asp Asn Cys Pro Xaa Gly
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Asn(CH2CHOHCH3)
<220> FEATURE:
<221> NAME/KEY: MOD_RES
<222> LOCATION: (8)
<223> OTHER INFORMATION: Orn

<400> SEQUENCE: 28

Cys Phe Ile Asn Asn Cys Pro Xaa Gly
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Asn(CH2CH2OCH2CH2OH)
<220> FEATURE:
<221> NAME/KEY: MOD_RES
<222> LOCATION: (8)
<223> OTHER INFORMATION: Orn

<400> SEQUENCE: 29
```

```
Cys Phe Ile Asn Asn Cys Pro Xaa Gly
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn

<400> SEQUENCE: 30

Cys Phe Ile Asn Asn Cys Pro Xaa Gly
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Asn(CH3)
<220> FEATURE:
<221> NAME/KEY: MOD_RES
<222> LOCATION: (8)
<223> OTHER INFORMATION: Dbu

<400> SEQUENCE: 31

Cys Phe Ile Asn Asn Cys Pro Xaa Gly
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Ala(2-Fur)
<220> FEATURE:
<221> NAME/KEY: MOD_RES
<222> LOCATION: (8)
<223> OTHER INFORMATION: Orn(i-Pr)

<400> SEQUENCE: 32

Cys Ala Ile Gln Asn Cys Pro Xaa Gly
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Thi
<220> FEATURE:
<221> NAME/KEY: MOD_RES
```

```
<222> LOCATION: (8)
<223> OTHER INFORMATION: Orn

<400> SEQUENCE: 33

Cys Xaa Ile Asn Asn Cys Pro Xaa Gly
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Thi
<220> FEATURE:
<221> NAME/KEY: MOD_RES
<222> LOCATION: (8)
<223> OTHER INFORMATION: Orn(i-Pr)

<400> SEQUENCE: 34

Cys Xaa Ile Gln Asn Cys Pro Xaa Gly
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: 3-Thi
<220> FEATURE:
<221> NAME/KEY: MOD_RES
<222> LOCATION: (8)
<223> OTHER INFORMATION: Orn

<400> SEQUENCE: 35

Cys Xaa Ile Asn Asn Cys Pro Xaa Gly
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Thi
<220> FEATURE:
<221> NAME/KEY: MOD_RES
<222> LOCATION: (8)
<223> OTHER INFORMATION: Dbu

<400> SEQUENCE: 36

Cys Xaa Ile Asn Asn Cys Pro Xaa Gly
1               5

<210> SEQ ID NO 37
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: 3-Thi
<220> FEATURE:
<221> NAME/KEY: MOD_RES
<222> LOCATION: (8)
<223> OTHER INFORMATION: Dbu

<400> SEQUENCE: 37

Cys Xaa Ile Asn Asn Cys Pro Xaa Gly
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Ala(2-Fur)
<220> FEATURE:
<221> NAME/KEY: MOD_RES
<222> LOCATION: (8)
<223> OTHER INFORMATION: Orn

<400> SEQUENCE: 38

Cys Ala Ile Asn Asn Cys Pro Xaa Gly
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn(CH3)

<400> SEQUENCE: 39

Cys Phe Ile Gln Asn Cys Pro Xaa Gly
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn(CH2CH2CH3)

<400> SEQUENCE: 40

Cys Phe Ile Gln Asn Cys Pro Xaa Gly
1               5

<210> SEQ ID NO 41
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn(i-Pr)

<400> SEQUENCE: 41

Cys Phe Ile Asn Asn Cys Pro Xaa Gly
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Ala(2-Fur)
<220> FEATURE:
<221> NAME/KEY: MOD_RES
<222> LOCATION: (8)
<223> OTHER INFORMATION: Orn(i-Pr)

<400> SEQUENCE: 42

Cys Ala Ile Asn Asn Cys Pro Xaa Gly
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Thi
<220> FEATURE:
<221> NAME/KEY: MOD_RES
<222> LOCATION: (8)
<223> OTHER INFORMATION: Orn(i-Pr)

<400> SEQUENCE: 43

Cys Xaa Ile Asn Asn Cys Pro Xaa Gly
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Ala(2-Fur)
<220> FEATURE:
<221> NAME/KEY: MOD_RES
<222> LOCATION: (8)
<223> OTHER INFORMATION: Dbu

<400> SEQUENCE: 44

Cys Ala Ile Asn Asn Cys Pro Xaa Gly
1               5

<210> SEQ ID NO 45
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn(i-Am)

<400> SEQUENCE: 45

Cys Phe Ile Gln Asn Cys Pro Xaa Gly
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn(CH3)

<400> SEQUENCE: 46

Cys Phe Ile Asn Asn Cys Pro Xaa Gly
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn(CH2CH3)

<400> SEQUENCE: 47

Cys Phe Ile Asn Asn Cys Pro Xaa Gly
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn

<400> SEQUENCE: 48

Cys Phe Ile Asn Asn Cys Pro Xaa Gly
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (4)
<223> OTHER INFORMATION: Asn(CH3)
<220> FEATURE:
<221> NAME/KEY: MOD_RES
<222> LOCATION: (8)
<223> OTHER INFORMATION: Orn

<400> SEQUENCE: 49

Cys Phe Ile Asn Asn Cys Pro Xaa Gly
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn(CH2CH2CH3)

<400> SEQUENCE: 50

Cys Phe Ile Asn Asn Cys Pro Xaa Gly
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn

<400> SEQUENCE: 51

Cys Phe Ile Gln Asn Cys Pro Xaa Gly
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Hmp
<220> FEATURE:
<221> NAME/KEY: MOD_RES
<222> LOCATION: (4)
<223> OTHER INFORMATION: Hgn
<220> FEATURE:
<221> NAME/KEY: MOD_RES
<222> LOCATION: (8)
<223> OTHER INFORMATION: Dbu(Abu)

<400> SEQUENCE: 52

Xaa Phe Ile Xaa Asn Cys Pro Xaa Gly
1               5

<210> SEQ ID NO 53
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (4)
<223> OTHER INFORMATION: Variable amino acid
<220> FEATURE:
<221> NAME/KEY: MOD_RES
<222> LOCATION: (8)
<223> OTHER INFORMATION: Variable amino acid
<220> FEATURE:
<223> OTHER INFORMATION: see specification as filed for detailed
      description of substitutions and preferred
      embodiments

<400> SEQUENCE: 53

Cys Xaa Ile Xaa Asn Cys Pro Xaa Gly
1               5
```